(12) United States Patent
Huang et al.

(10) Patent No.: US 10,562,020 B2
(45) Date of Patent: Feb. 18, 2020

(54) METHOD FOR MANUFACTURING ENVIRONMENT-CONTROLLING FIBERS

(71) Applicants: Kai-Li Huang, Taichung (TW);
Yuan-Te Chen, Taichung (TW);
Yuan-Jung Chen, Taichung (TW)

(72) Inventors: Kai-Li Huang, Taichung (TW);
Yuan-Te Chen, Taichung (TW);
Yuan-Jung Chen, Taichung (TW)

(*) Notice: Subject to any disclaimer, the term of this patent is extended or adjusted under 35 U.S.C. 154(b) by 397 days.

(21) Appl. No.: 15/513,876

(22) PCT Filed: Sep. 24, 2014

(86) PCT No.: PCT/CN2014/087310
§ 371 (c)(1),
(2) Date: Mar. 23, 2017

(87) PCT Pub. No.: WO2016/045013
PCT Pub. Date: Mar. 31, 2016

(65) Prior Publication Data
US 2017/0282173 A1    Oct. 5, 2017

(51) Int. Cl.
*D01D 1/04* (2006.01)
*D01D 5/08* (2006.01)
(Continued)

(52) U.S. Cl.
CPC .............. *B01J 35/06* (2013.01); *A01G 9/20* (2013.01); *A01G 22/00* (2018.02); *A01N 25/34* (2013.01); *A01N 65/08* (2013.01); *A01N 65/28* (2013.01); *A01N 65/36* (2013.01); *B01J 23/66* (2013.01); *B01J 35/004* (2013.01); *B01J 35/0093* (2013.01); *C08L 23/00* (2013.01); *C08L 23/12* (2013.01); *C09K 11/02* (2013.01); *C09K 11/7792* (2013.01); *D01F 1/10* (2013.01); *D01F 6/04* (2013.01); *D01F 6/46* (2013.01); *D06N 7/00* (2013.01); *C08L 2203/12* (2013.01);
(Continued)

(58) Field of Classification Search
CPC .... D01D 1/04; D01D 5/08; D01F 1/02; D01F 1/07; D01F 1/09; D01F 1/10; D01F 6/04; D01F 6/06
USPC .......................... 264/21, 104, 105, 210.6, 211
See application file for complete search history.

(56) References Cited

FOREIGN PATENT DOCUMENTS

CN      1766184 A  *  5/2006
CN    102380908 A  *  3/2012

OTHER PUBLICATIONS

Machine Translation CN 1766184 A (Year: 2006).*
Machine Translation CN 102380980 A (Year: 2012).*

* cited by examiner

*Primary Examiner* — Leo B Tentoni (57) ABSTRACT

The invention discloses environment-controlling fibers, method manufacturing the same and fabrics using the same, which adopts polyolefin material, optoelectronic material, thermoelectric material, piezoelectric material and catalyst material, to make fibers and fabric by melting, mixing, drawing and weaving. The fabrics are used in all kinds of environmental control products or for organic agriculture. To use green energy such as solar light energy, solar thermal energy, wind energy, hydro energy, geothermal energy and other renewable energy to stimulate the function of the special material within the fibers, so that the fabrics can remove pollutants in the environment and produce self-purification function to achieve the purpose of improving the environmental conditions or promote plant growth.

9 Claims, 5 Drawing Sheets

(51) Int. Cl.
*D01F 1/02* (2006.01)
*D01F 1/09* (2006.01)
*D01F 6/06* (2006.01)
*B01J 35/06* (2006.01)
*C08L 23/00* (2006.01)
*D01F 1/10* (2006.01)
*D01F 6/04* (2006.01)
*A01G 22/00* (2018.01)
*A01G 9/20* (2006.01)
*A01N 25/34* (2006.01)
*A01N 65/08* (2009.01)
*A01N 65/28* (2009.01)
*A01N 65/36* (2009.01)
*B01J 23/66* (2006.01)
*B01J 35/00* (2006.01)
*C08L 23/12* (2006.01)
*C09K 11/02* (2006.01)
*C09K 11/77* (2006.01)
*D01F 6/46* (2006.01)
*D06N 7/00* (2006.01)
*D01F 1/07* (2006.01)
*H01L 41/08* (2006.01)

(52) U.S. Cl.
CPC ............... *D01F 1/07* (2013.01); *D01F 1/103* (2013.01); *D01F 1/106* (2013.01); *D10B 2401/13* (2013.01); *D10B 2401/16* (2013.01); *D10B 2505/18* (2013.01); *H01L 41/082* (2013.01)

METHOD FOR MANUFACTURING ENVIRONMENT-CONTROLLING FIBERS

FIELD OF INVENTION

The invention relates to fibers for controlling environment by green energy, method manufacturing the same and fabrics made by the same, which are applied to form organic environments for the farming industry such as the green energy control greenhouse and the green energy control factory for agricultural plant, or applied to environmental control equipment for the life such as the fabrics for environment control by green energy for health cares, for promoting the indoor air quality, for filtering fumes, for geotextile for planting, for removing fog, for cleaning the air, and for environmental pollution control. Using the environmental energy, such as solar energy, solar heat energy, wind energy, hydro energy, geothermal energy and other renewable energy, the fiber materials receive the various types of radiation of green energy to produce free electronic effects, through the fibers composed of optoelectronic materials, thermoelectric materials and piezoelectric materials having increasing effects on the natural energy of green energy radiated waves thus to act on various kinds of catalyst materials in fibers and effectively promote the functions of catalyst materials, so that the catalyst fibers and fabrics produce favorable lights, water oxygen anion or far-infrared light by the green energies to control pests and diseases, and to remove, settle, decompose and clean the pollutants to have a good environment for plant growth.

BACKGROUND

In response to the increasing demand for food and the food crisis, human beings have tried to increase food production by using various agricultural methods such as genetically modified, chemical pesticides, chemical fertilizers and growth hormones, and microbial fertilizers. In order to solve the problem of food demand and food crisis, the above-mentioned agricultural methods are also accompanied by a large number of pesticide uses, so that environmental pollution is becoming increasingly serious. The poor environment caused by pollution is directly to human health damage, and later accompanying with climate change and the increase in new pests and diseases of plant, but also reduce crop yields. Under the vicious cycle of soil acidification, the food crisis has not been fundamentally lifted. The requirements of increase of production and organic planting, result in problems to be overcome for the quality and quantity of agricultural environment and crops. Good natural environment resources are limited, in order to sustainable development of agriculture, fundamentally solve the problem of human food shortage and improve food safety and health, so human beings should learn the nature of the natural environment of endless natural circulation principle. To sustainably use the green energies, maximize the effectiveness of transformation of the green energies, to use the principle of natural interaction between material properties and the green energies, by the natural way can create a suitable control for organic environment for agricultural productions, so as to have the opportunity to fundamentally solve the aforementioned problems of vicious cycle caused by traditional agricultural processes and to meet the requirement and safety for food.

Although known techniques include the addition of functional materials such as catalysts to the fabric, the function of deodorizing and antibacterial will be produced by the action of the catalyst material. However, one of the known techniques is to coat functional materials on the surface of the fabric, not only the functional material can't be effectively increased to play its effectiveness, and after a period of time it will fall off, so the economic benefits of such technology is not high. Other techniques, such as U.S. Pat. No. 4,784,909 discloses fiber added with copper so as to produce the function of antibacterial deodorization. For another example, U.S. Pat. No. 6,540,807 discloses fabric added with thermoplastic resin and antibacterial agent to have antibacterial function. For another example, the U.S. Pat. No. 5,690,922 discloses the fiber added with metal phosphate and metal hydroxide to have deodorant function. However, the previously known traditional techniques, functional materials in fibers only can act in a limited effective space because they are not effectively amplified. Moreover, although the industry develop LED lights emitting blue and red light to promote the growth of fruits and vegetables for the cultivation, but the use of LED lights needs electric power and expensive equipment, relatively results in high cost, and not only result in the problems of energy consumption, and can't control pests and diseases of plant, but also finally the cultivation must still rely on pesticides or biological control, or needs to install net to isolate pest, closed plastic shed and glass greenhouse, etc. which can't reach effective control for environment.

Therefore, in order to achieve effective control of agricultural production and energy conservation, the present inventors believe that it is necessary to make use of the green energy source which exists in nature and endlessly to convert the green energy and create a suitable crop growth environment. Such as the use of green energy, the use of the sunlight one kind of the green energy, and the use by converting and amplifying the sunlight into light waves required for the plant growth, will increase the organic crop production in network rooms. Through the energy band effect of crystal in the fiber material, the fiber material receives the green energy and amplifies the performance of the catalyst material in the fiber material, not only convert the sunlight and increase the required light, but minimizes the humidity of air, which is conducive to plant growth, and can prevent plant diseases and remove pollutants in the environment. Moreover, the fiber material can be used with natural plant essential oils to avoid the pests, and thus achieve the purpose of a large number of organic cultivation. The above is the concept of the present invention, the motivation of research and development for the inventor, and is also worthy to research and develop the agricultural materials for green energy control, and can really achieve organic agriculture planting and environmental pollution control, so as to really improve the problems of the current traditional organic agricultural materials for environmental control and the problem of energy consumption for food production.

SUMMARY OF THE INVENTION

The first object of the present invention is to provide environment-controlling fibers and fabrics having the functions of controlling environment by using green energy to increase the growth of organic agricultural plants. To use the special material properties of the environment-controlling fibers can increase the plant-growth-required light wave, transfer the harmful light waves or increase the time of exposure of light, decompose moisture in the air to minimize water molecules (water oxygen anion) to promote effectiveness of absorption of water, produce far-infrared light to provide plants with required lights and remove pollutants in the environment, so as to upgrade the effectiveness of sun, water, air and soil on the quality and quantity of the organic plant production. The technical means of the present invention is that the fiber is made of polyolefin material as the base material. The polyolefin material is mixed with optoelectronic material (material having function of converting sunlight to be long-lasting fluorescent or/and phosphorescent) having the function of optoelectronic effect for light conversion and storage, piezoelectric material having the function of piezoelectric effect by coupling the stress field and the electric field, thermoelectric material capable of receiving external heat radiation to produce far infrared rays, and catalyst material capable of accelerating the chemical reaction rate. When the fiber receives the outside green energy, such as solar energy, through the effectiveness of optoelectronic material (such as the material having the function for accumulating long-lasting fluorescent or/and phosphorescent) can produce spectrum (wavelength about 400~700 nm) required by plant growth, converse harmful UV light to be the light with wavelength of 400~700 nm required for the growth of plants, and storage the light energy for the plant to grow at night to promote plant growth. When the fiber receives outside green energies such as solar thermal energy or geothermal energy, through the effectiveness of thermoelectric materials, it can produce infrared energy amplitude with a wavelength of 4~14 μm in the environment to promote the growth of plants. When the fiber receives the outside of the green energy such as wind energy, through the effectiveness of piezoelectric material, it can produce piezoelectricity in the environment to decompose the hydraulic energy of air humidity to produce water oxygen anion and form an environment like rain forest ecology, and promote the effectiveness of water absorption of the plants. The catalytic material is resonated by the optoelectronic effect, the thermoelectric effect and the piezoelectric effect to amplify the amplitude of energies to activate the free electrons, and to increase the catalysis activity of the electron and electron-hole at a bigger energy amplitude level in the material, so that the catalysis activity of the catalyst material is increased to have more effectiveness to remove environmental pollutants.

The second object of the present invention is to provide environment-controlling fibers and fabrics having the functions to remove the biological contaminant. The technical means of the present invention are the fibers as above-mentioned first purpose mixed with the catalyst material which can remove the biological pollutants in the environment. Through equipping with the catalyst material, the fibers and their fabrics have the function of restraining the source of biological pollution in the environment, and thus achieve the effectiveness and purpose of restraining the pollution sources such as fungi, bacteria and viruses in the environment.

The third object of the present invention is to provide environment-controlling fibers and fabrics having the functions to remove the chemical contaminant in the environment. The technical means of the present invention are the fibers as above-mentioned first purpose mixed with catalyst material which can remove chemical contaminants, and can remove formaldehyde (HCHO), the total volatile organic compounds (TVOCs), carbon monoxide (CO), carbon dioxide ($CO_2$), ozone ($O_3$), acetic acid, acetaldehyde, ammonia, positive and negative ions ($F^-$, $Cl^-$, $NO^{3-}$, $PO_4^{3-}$, $SO_4^{2-}$, $NH_4^+$) and other chemical pollutants in the environment.

The fourth object of the present invention is to provide environment-controlling fibers and fabrics having the functions to remove physical contaminant in the environment. The technical means of the present invention are the fibers as above-mentioned first purpose mixed with catalyst material which can settle physical pollution sources in the environment, and can settle the physical pollution sources from air to the ground, such as pollen, $PM_{2.5}$, $PM_{10}$ and other suspended particles.

The fifth object of the present invention is to provide environment-controlling fibers and fabrics having phytoncide for pest control. The technical means of the present invention are the fibers as above-mentioned four purposes respectively mixed with natural plant essential oils which can control and avoid from insects, and can produce plant phytoncide to facilitate plant growth.

The sixth object of the present invention is to provide safety environment-controlling fibers and fabrics having the function of flame resistant and conductive antistatic. The technical means of the present invention are the fibers as above-mentioned five projects mixed with fireproof materials and conductive antistatic the material to have safety function.

The seventh object of the present invention is to provide woven fabrics applied with the environment-controlling fibers of the present invention. The woven fabrics can be woven fabrics used to assist the cultivation for plants, can be woven fabrics used by the plant factory, can be woven fabrics as gratings for plant growth, can be woven fabrics used by various types of environmental control equipment for the life, can be woven fabrics used for health care, can be woven fabrics used to promote quality of indoor air, can be woven fabrics used to filter fumes, can be woven fabrics as geotextiles, can be woven fabrics used to remove fog, can be woven fabrics to clean air, or can be woven fabrics for controlling environmental pollution.

DETAILED DESCRIPTION OF THE PREFERRED EMBODIMENT

Figure 5:
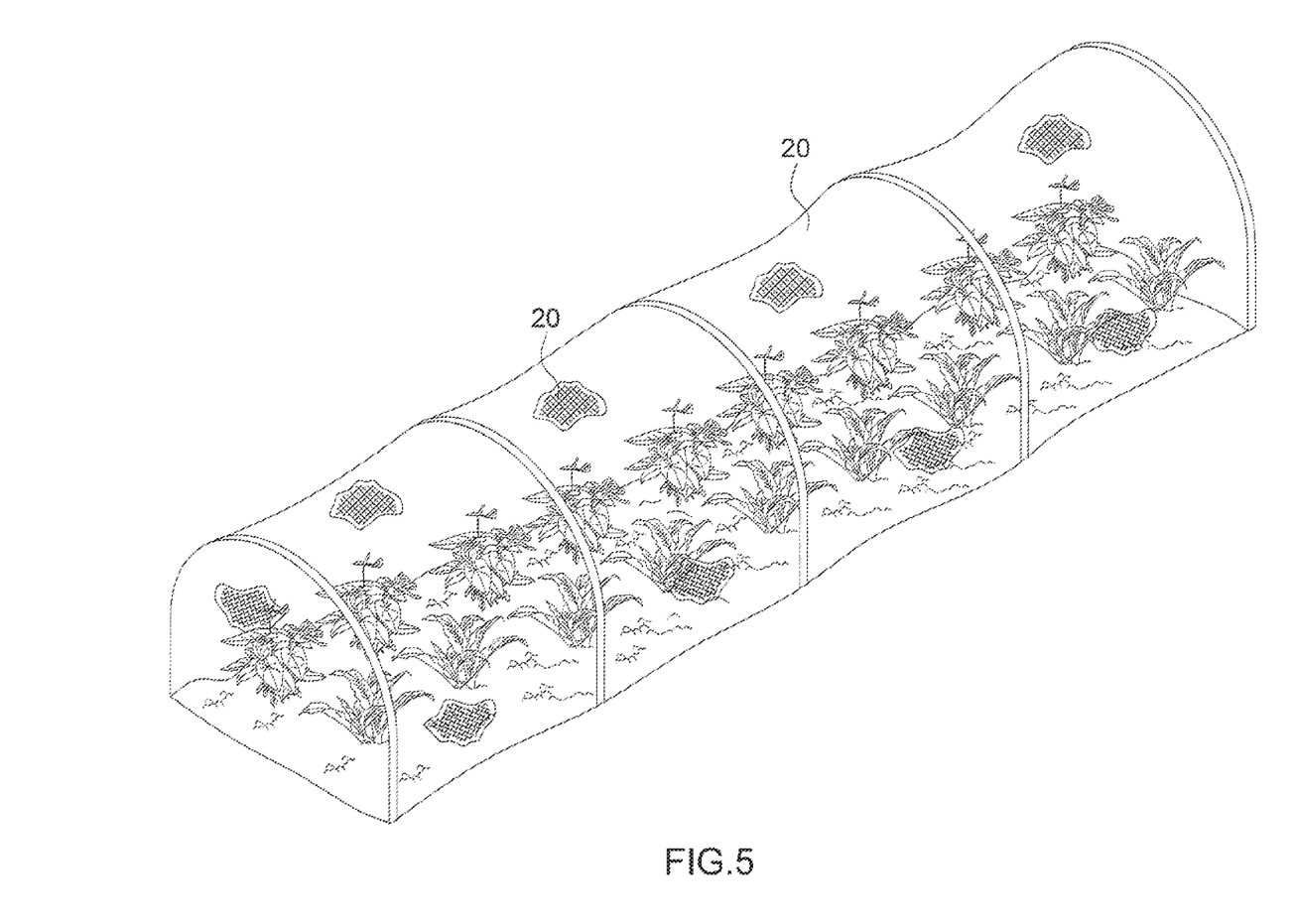
FIG. 5 is a schematic view of woven fabric for agriculture of the present invention.

The environment-controlling fiber developed by the present invention has the energy transmission ability when the fiber receives the outside green energy. The fibers produces optoelectronicity through the optoelectronic material, produces piezoelectricity through the piezoelectric material, and produces resonant effect through the thermoelectric material (far-infrared ray material) to increase the amplitude and activation of energy to excite the catalyst material, so as to increase catalytic effect on the activity of electron and electronic hole at the energy level, and effectively enhance the catalytic performance of catalyst to catalytic and control the environmental pollutant, and produce light with wavelength of 400~700 nm (such as the far-infrared ray with the wavelength of 4~14 μm) and decompose water in the air (humidity) to produce water oxygen anion. Thus, the woven fabric 20 woven by the fibers of the present invention has the function of increasing the effect by resonance and friction so as to produce an environmental control function, and the woven fabric 20 can be used for organic agriculture, or gratings for plant growth (referring to FIG. 5). Moreover, the woven fabric 20 of the present invention can be used for health cares, for promoting the indoor air quality (such as fabric filter for air conditioner), equipped on the device for filtering fumes (such as fabric filter for filtering fumes), as geotextile for planting (such as geotextile pad bedding under or on the soil for planting), for removing fog (such as fabric filter equipped on washing tower for removing fog), for cleaning air (such as fabric filter for cleaning air), for changing air (such as window screen), and for environmental pollution control (such as the filter of industrial water washing equipment for producing positive and negative ions to remove TVOCS. The basic characteristics of the technology for fiber of the present invention is mixing the polyolefin (such as polypropylene and polyethylene, etc., by the hydrocarbon materials to reduce the environmental pollution) with optoelectronic materials, piezoelectric materials, thermoelectric materials and catalyst Materials, by an air-cooled granulation equipment with twin-screw, the above materials were melted, mixed and granulated to be granular processing materials, and then melting the granular processing materials and drawing to be fibers by a melt drawing processing technology. So the woven fabric by the fibers of the present invention receives external sunlight, air flow, heat, energy of vibration and friction of fibers, air humidity and other natural energy, through the optoelectronic materials to produce optoelectronicity, piezoelectric material to produce piezoelectric effect and through thermoelectric materials to produce thermoelectric effect (produce far-infrared ray). Through the thermoelectric effect, the piezoelectric effect, the photocatalytic effect, the redox effect, the free electron effect, the catalytic effect and the slow release to amplify the natural energy and apply to the catalyst materials, the catalyst materials can fully exert its effectiveness. The ratio of weight of each material can be adjusted according to the requirement of the user. The main concept of the invention is to integrate the optoelectronic material, the piezoelectric material, the thermoelectric material and the catalyst material to the fiber so that when the fiber receives the natural energy, the catalyst material in the medium can produce the increasing of amplitude of effect. First, the fibers of fabrics can produce far-infrared ray with wavelength range of 4~14 μm and decompose water of moisture (humidity) to produce water oxygen anion. Second, the fibers of fabrics can produce light effect to increase plant growth and limit the wavelength of sunlight at 400~700 nm, and increase the long afterglow for the night brightness. Third, the fibers of fabrics can inhibit the biological pollution sources such as the total bacteria and mold in the air to reduce plant diseases. Fourth, the fibers of fabrics can reduce chemical pollution source in the air (such as air vapor pollutants: HCHO, TVOCs, $O_3$, CO, $CO_2$, $SO_X$, $NO_X$, $C_XH_Y$, HCl, $CS_2$, $CFC_S$ and $C_mH_nX_x$, etc.), or can settle the physical pollution in the air such as airborne particulate pollen, $PM_{2.5}$, $PM_{10}$ and other suspended particles. Fifth, the fibers of fabrics can avoid insects so that plants prevent from pest hazards and infectious bacteria. Sixth, the fibers of fabrics have the safety functions of fireproof and anti-static by conductive. The environment-controlling fiber of the present invention has excellent performance function, which can be used for weaving fabric to be applied to agriculture for environmental control by the green energies such as applied to greenhouse room, gratings for plant growth and the like, and can be applied to all kinds of equipment for environmental control by green energy such as fabrics for health care, for promoting the quality of indoor, for filtering oil smoke, for removing fog, for planting such as geotextile, for cleaning air, applied to be window screen and for controlling environmental pollution, i.e. for widely used by agriculture, industry, fisheries, animal husbandry and the people's livelihood.

The optoelectronic effect of the optoelectronic material used in the preset invention is that when the electromagnetic radiation (such as ultraviolet light) irradiates to the optoelectronic material, the photon is absorbed to excite the free electron. The optoelectronic material is mainly the material can receive sunlight and convert the light to be fluorescent or/and phosphorescence, and store them for long-lasting, and such material basically is $Zn_2SiO_4$, $CaSiO_3$, $SiO_2$, $TiO_2$, $(SrBaMg)_3Si_2O_7$, $CaWO_4$, $MgWO_4$, $LiAl_5O_8:Mn^{4+}$, $CaAl_2O_4:Eu^{2+}$, $Dy^{3+}$, $CaAl_{12}O_{19}:Mn^{4+}$, $SrAl_2O_4:Eu^{2+}$, $Dy^{3+}$, $Sr_4Al_{14}O_{25}:Eu^{2+}$, $Dy^{3+}$, $SrAl_{12}O_{19}:Eu^{2+}$, $Dy^{3+}$, $BaMg_2Al_{16}O_{27}$, $CeMgAl_{11}O_{19}$, $MgAl_2O_4$, $GdAlO_3$, $Y_2O_3$, $YVO_4$, $SrB_4O_7F$, $MgGa_2O_4$, $MgGa_2O_4$, BeO, MgO, $Al_2O_3$, $GeO_2SnO_2ZnO$, $Sc_2O_3$, $La_2O_3$, $Sm_2O_3$, $Gd_2O_3$, $Dy_2O_3$, $ZrO_2$, CdS or $WO_3$.

The piezoelectric effect of the piezoelectric material used in the present invention is that the atoms are specially arranged in the lattice of the piezoelectric material so as to have coupling effect between the stress field and the electric field. The piezoelectric material is basically quartz, cadmium sulfide, zinc oxide, aluminum nitride, ferroelectric crystal, barium titanate crystal, lithium niobate, tantalum niobate, barium niobate crystal, potassium dihydrogen phosphate, ammonium dihydrogen phosphate, lead hydrogen phosphate, deuterium lead phosphate, bismuth titanate crystals, barium titanate ceramics, lead zirconate titanate PZT, and the like.

The thermoelectric material used in the present invention is the far-infrared rays producing material for receiving external thermal radiation to produce far-infrared rays with the spectrum of 4-14 μm wavelength which is greater than the wavelength of visible light and has strong heat effect of heat sensing energy. The thermoelectric material is basically $Al_2O_3$, $ZrO_2$, MgO, $TiO_2$, $SiO_2$, ZrC, SiC, $B_4C$, TaC, $TiB_2$, $ZrB_2$, $CrB_2$, $TiSi_2$, $MoSi_2$, $WSi_2$, $Si_3N_4$, TiN, $Fe_2O$, high temperature bamboo charcoal, prepared long charcoal, Maifan stone, Guiyang stone, volcanic rocks or jade.

The catalyst material used in the present invention is catalyst agent which provides another reaction path by a lower activation energy and is capable of accelerating the chemical reaction rate, and is the substance with the quality, composition and chemical properties remaining unchanged before and after the chemical reaction. The catalyst material can be catalyst metal, such as gold, platinum, palladium, silver, iron, copper, titanium, nickel, tungsten, zinc, manganese, germanium, bismuth, ruthenium, osmium, iridium, molybdenum, praseodymium, neodymium, promethium or carbon nanotubes. The catalyst material can be oxidized metal catalyst, such as germanium oxide, zinc oxide, silicon oxide, titanium oxide, alumina, iron oxide, palladium oxide, magnesium oxide, zirconium oxide, nickel oxide, tin oxide, manganese oxide, Chromium oxide, cerium oxide, neodymium oxide or yttrium oxide.

The natural plant essential oil used in the present invention can be tea tree oil, neem leave oil, lemon oil, methyl salicylate oil, camphor oil, clove oil, peppermint oil, eucalyptus citriodora oil, citronella oil, cubeb litsea oil, salvia officinalis oil, eucalyptus oil, rose oil, jasmine oil, geranium oil, rose geranium oil, ylang oil, frankincense oil, patchouli oil, rosemary oil, helichrysum oil, thyme oil, pine oil, cedar oil, cade oil, sandal wood oil, *Ocimum basilicum* oil, lime oil, orange *Citrus sinensis* oil, bitter orange oil, bitter orange leaf oil, orange flower oil, chamomile oil, myrrh oil, amaranth oil, white Melaleuca oil, ginger oil and so on.

The flame retardant and fireproof material is antimony trioxide, magnesium hydroxide, red phosphorus, molybdenum compound, zinc borate, zinc stannate, decabromodiphenyl oxide, octabromo-ether, organic silicon or carbon black.

The conductive antistatic material used in the present invention is polyether, quaternary ammonium salt, sulfonate, betaine, conductive carbon black, carbon fiber, metal fiber, nickel-plated metal carbon fiber or nano carbon tube.

Figure 4:
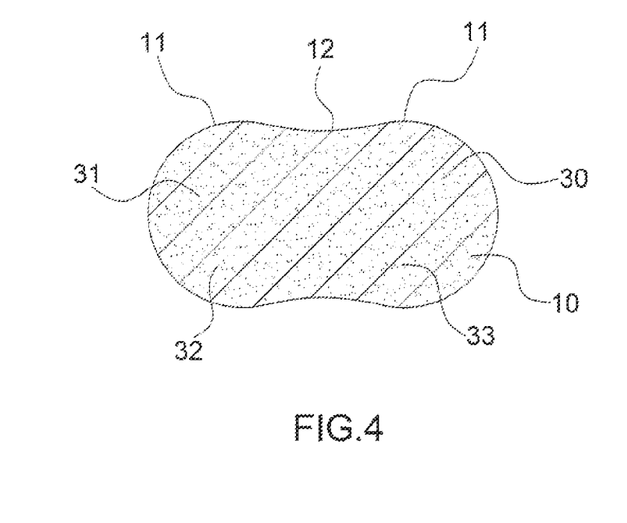
FIG. 4 is a schematic view of cross-sectioned of fiber of the present invention.

The basic characteristics of the environment-controlling fiber of the invention are that the material is mixing the polyolefin with optoelectronic materials, piezoelectric materials, thermoelectric materials and catalyst materials, adding rubber elastic material (such as Ethylene-Propylene-Diene Monomer, EPDM) whether or not determined by the ratio of each other material and the requirement of strength, by an air-cooled granulation equipment with twin-screw, the above materials were melted, mixed and granulated to be granular processing materials, and then melting the granular processing materials and drawing to be fibers each with Danni number of 50~50000 den by a melt drawing processing technology. Wherein, the polyolefin may be polypropylene having a melt flow rate (MFR) in the range of 0.1~50 g/10 min, or may be polyethylene having a melt flow rate (MFR) in the range of 0.1~50 g/10 min. The characteristic of the optoelectronic material is light storage (0.3~0.32 mcd/m$^2$), and whose particle size distributing at 10 nm~0.1 µm. The piezoelectric material has the following characteristics: the piezoelectric coefficient is ($10^{-12}$C/N) 0.1~1000, and the particle size distributing at 10 nm~0.1 µm. The characteristics of thermoelectric materials are: the emissivity of far-infrared ray with wavelength range of 4~14 µm is 0.85~0.99%, and the particle size distribution is 10 nm~0.1 µm. The EPDM has a Mooney viscosity (ML1+4, 125 degrees Celsius) of 20~70. As shown in FIG. 4, in a preferred embodiment, the surface of the fiber 10 is integrally formed with at least two ridges 11 viewed from the cross section of the fiber 10, the length of the ridges 11 extend along the axial direction of the fiber 10, the top of the ridges 11 extending in a curve, and the two ridges 11 are smoothly connected with a Curved depression 12. When the fiber receive external sunlight, through the interactions of the optoelectronic material 30, piezoelectric material 31, thermoelectric material 32 and catalyst material 33, the sunlight will be converted to required color light for plant growth, the curvatures of the ridges 11 scatter the color light out to the plant to promote plant growth.

Figure 1:
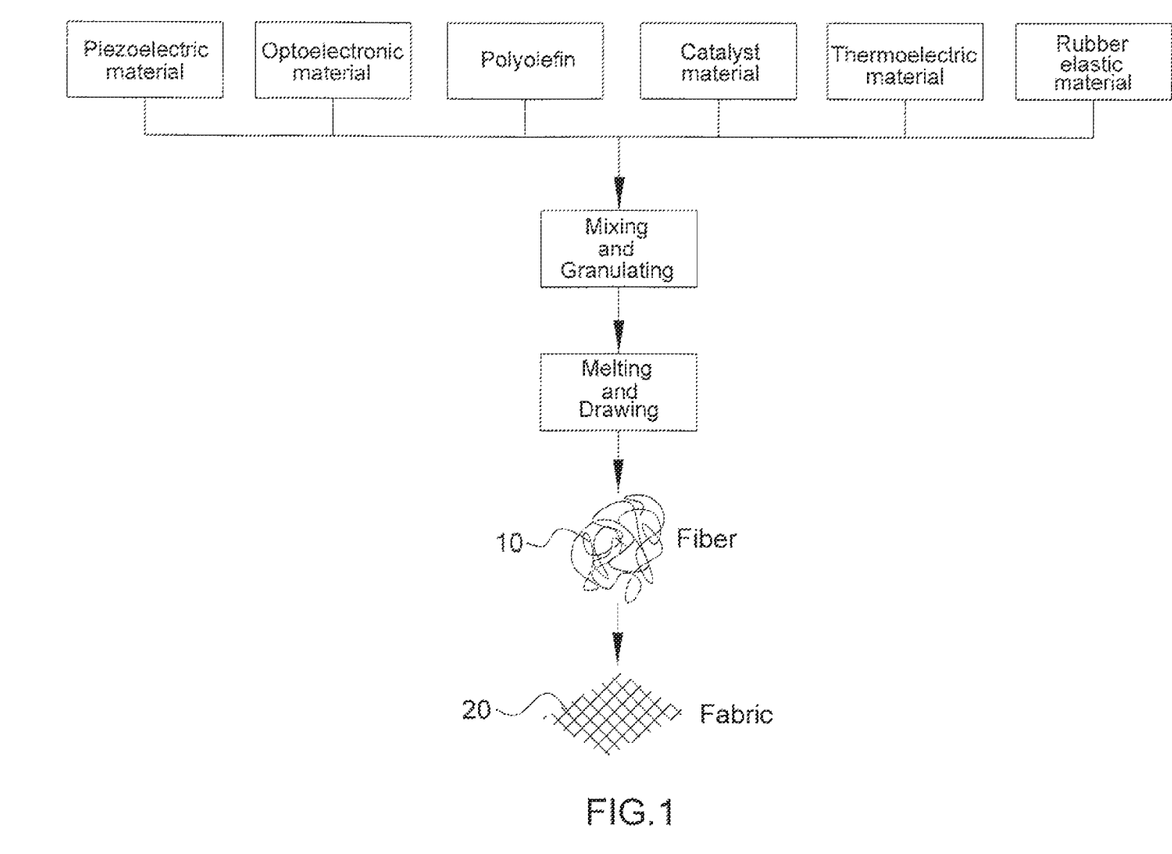
FIG. 1 is a schematic view of a first embodiment of the manufacturing method of the present invention.

As shown in FIG. 1, the basic characteristics of the method for producing the environment-controlling fiber to achieve the above-mentioned first to fourth objects of the present invention are mainly preparing polyolefin by weight of 70~95% as a base material, such as polypropylene chips or polyethylene chips (melt flow rate, MFR is in the range of 0.1~50 g/10 min) (the following corresponding examples of the present invention are preparing polypropylene having a melt flow rate of 5 g/10 min and by weight ratio of 70% or 80%), preparing optoelectronic material by weight ratio of 1~10% (the following examples of the present invention are exemplified the optoelectronic material by weight ratio of 10% and with particle size distribution of 0.3 µm), preparing piezoelectric material by weight ratio of 1~5% (the following examples of the present invention are exemplified the piezoelectric material by weight ratio of 2% and with particle size distribution of 1 µm), preparing thermoelectric material by weight ratio of 1~5% (the following examples of the present invention are exemplified the thermoelectric material by weight ratio of 2% with particle size distribution of 1 µm), preparing catalyst material by weight ratio of 1~5% (the following examples of the present invention are exemplified the catalyst material by weight ratio of 3% with particle size distribution of 0.3 µm), and depending on requirement for the ductility, strength and hardness of the fiber to choose whether to add rubber elastic material (such as Ethylene-Diene Monomer, EPDM) (the following examples of the present invention are illustrated by taking EPDM by weight ratio of 3% with Mooney viscosity of 60). The above-mentioned materials were melted and mixed by the air-cooled granulation equipment with twin-screw, and were granulated to be granular processing materials, and then melting the granular processing materials and drawing to be fibers each with Danni number of 50~50000 den by a melt drawing processing technology, wherein the granulation temperature is 160~250 degrees Celsius in gradually increasing mode when using polypropylene as the base material, the granulation temperature is 260~350 degrees Celsius in gradually increasing mode when using polyethylene as the base material, the plurality of granular processing materials were made with the average particle diameter less than 2~10 mm, and the plurality of granular processing materials are to be formed fibers by spinning, cooling, thermally stretching and heating through a single screw extruder. Wherein when the polypropylene is used as the base material, the spinning temperature is 160~250 degrees Celsius in gradually increasing mode, and when the polyethylene is used as base material, the spinning temperature is 160~350 degrees Celsius in gradually increasing mode, the later cooling temperature is 20~50 degrees Celsius, the drawing times rate is 3~8 times, the hot water extension temperature of 80~120 degrees Celsius, and the winding speed is 40~180 rpm. If polypropylene was used as base material in the embodiment of the present invention, the granulation temperature was gradually increased by 180/200/210/220/230/240 degrees Celsius, the fiber spinning temperature was gradually increased by 200/210/220/230/240/250 degrees Celsius, the cooling temperature was 25 degrees Celsius, the hot water extension temperature was 100 degrees Celsius, the drawing times ratio is 6 times and the winding speed is 120 rpm. The melt drawing processing technology is carried out by heating and melting the granular processing material, extruding it into the cooling water from the spinneret, cooling it in the cooling water and winding at a constant speed at the same time, then hot stretching and winding by several times of speed in hot water, at this stage of the processing of minimizing and solidifying the molten material at the same time resulting in the fiber formed, then winding the finished fiber.

Figure 2:
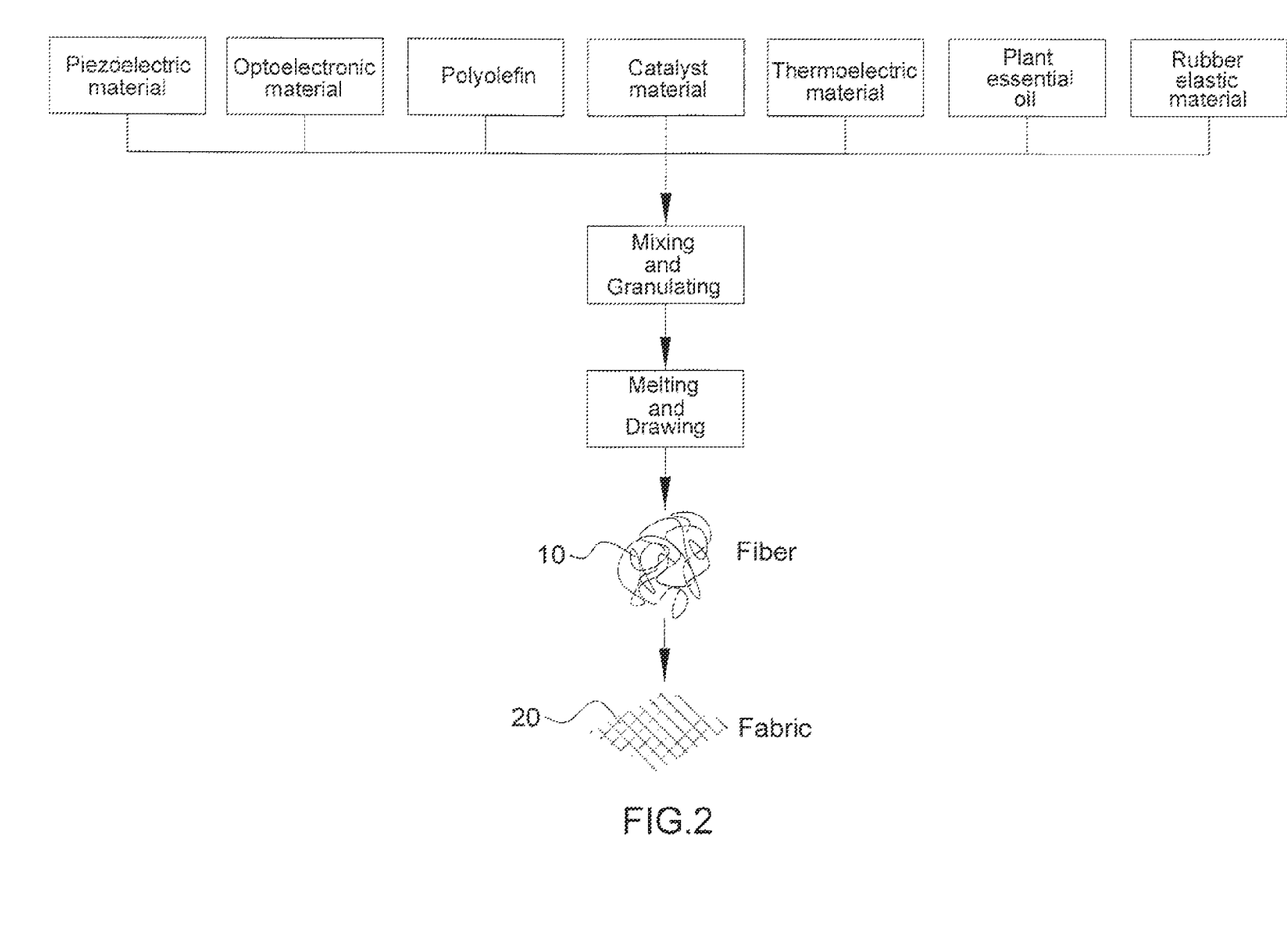
FIG. 2 is a schematic view of a second embodiment of the manufacturing method of the present invention.

As shown in FIG. 2, the basic characteristics of the method for producing the environment-controlling fiber to achieve the above-mentioned fifth object of the present invention are mainly using polyolefin by weight of 65~94% as a base material (the following corresponding example of the present invention is preparing polypropylene having a melt flow rate of 5 g/10 min and by weight ratio of 80%), using functional material by weight ratio of 5~25% including optoelectronic material by weight ratio of 1~5%, piezoelectric material by weight ratio of 1~5%, thermoelectric material by weight ratio of 1~5%, catalyst material by weight ratio of 1~5% and rubber elastic material by weight ratio of 1~5% (in one embodiment of the present invention, the optoelectronic material is by weight ratio of 2% with particle size distribution of 0.3 µm, the piezoelectric material is by weight ratio of 2% with particle size distribution of 1 µm, the thermoelectric material is by weight ratio of 2% with particle size distribution of 1 µm, the catalyst material by weight ratio of 3% with particle size distribution of 0.3 µm, and the rubber elastic material (EPDM) by weight ratio of 3% with Mooney viscosity of 60, i.e. the functional material is by weight ratio of 12% including optoelectronic material, piezoelectric material, thermoelectric material, catalyst material and EPDM), and using natural plant essential oils by weight ratio of 1~10% (the following corresponding test example of the present invention is preparing natural plant essential oils by weight ratio of 8%).

Figure 3:
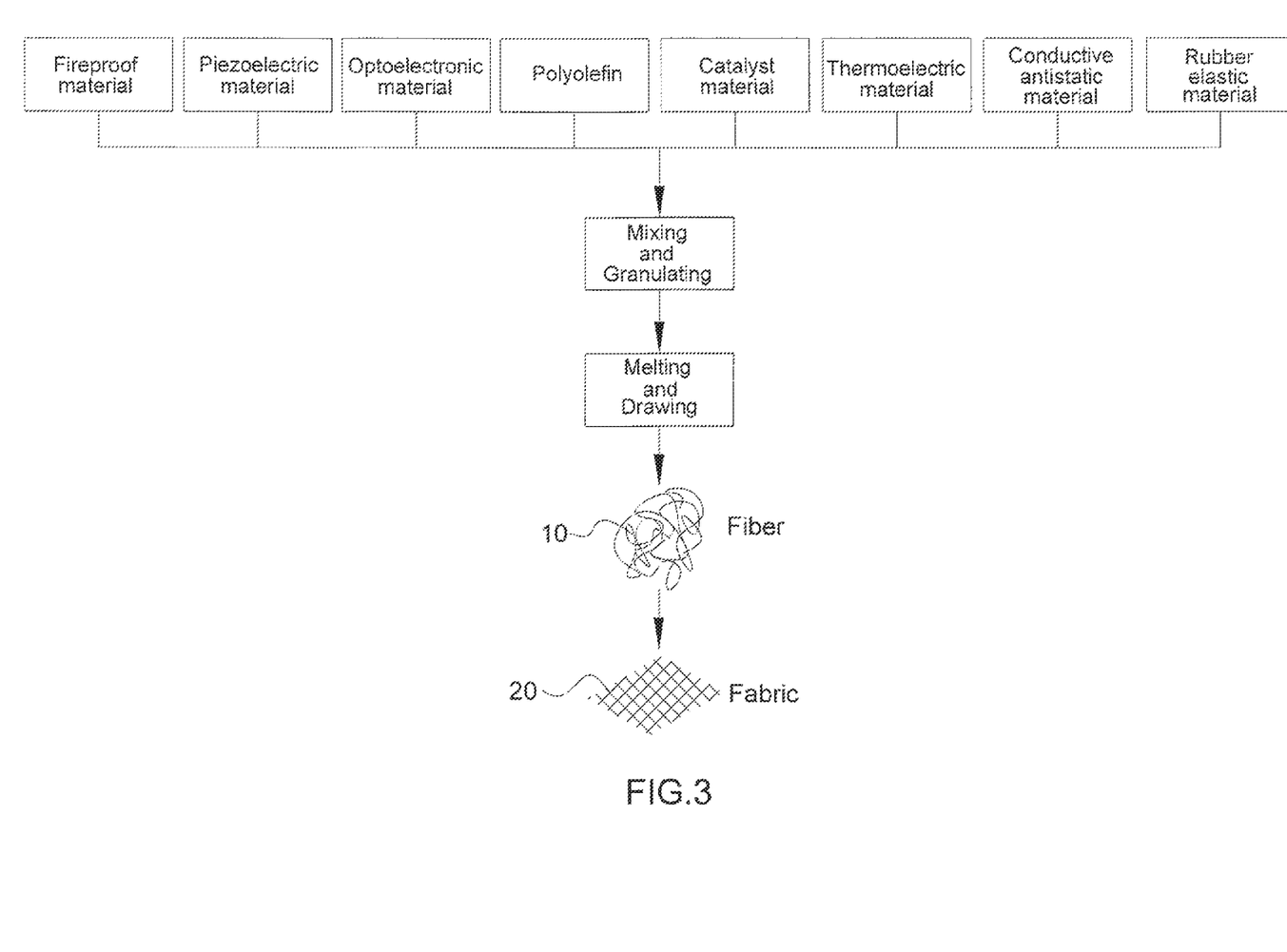
FIG. 3 is a schematic view of a third embodiment of the manufacturing method of the present invention.

As shown in FIG. 3, the basic characteristics of the method for producing the environment-controlling fiber to achieve the above-mentioned sixth object of the present invention are mainly using polyolefin by weight of 55~92% as a base material (the following corresponding example of the present invention is preparing polypropylene having a melt flow rate of 5 g/10 min and by weight ratio of 70%), using functional material by weight ratio of 5~25% including optoelectronic material by weight ratio of 1~5%, piezoelectric material by weight ratio of 1~5%, thermoelectric material by weight ratio of 1~5%, catalyst material by weight ratio of 1~5% and rubber elastic material by weight ratio of 1~5% (in one embodiment of the present invention, the optoelectronic material is by weight ratio of 2% with particle size distribution of 0.3 µm, the piezoelectric material is by weight ratio of 2% with particle size distribution of 1 µm, the thermoelectric material is by weight ratio of 2% with particle size distribution of 1 µm, the catalyst material by weight ratio of 3% with particle size distribution of 0.3 µm, and the rubber elastic material (EPDM) by weight ratio of 3% with Mooney viscosity of 60, i.e. the functional material is by weight ratio of 12% including optoelectronic material, piezoelectric material, thermoelectric material, catalyst material and EPDM), using natural plant essential oils by weight ratio of 1~5% (the following corresponding test example of the present invention is preparing natural plant essential oils by weight ratio of 3%), using fireproof material by weight ratio of 1~10% with particle size distribution of 10 nm~0.1 µm (the following examples of the present invention are illustrated by using fireproof material by weight of 10%), and using the conductive antistatic material by weight ratio of 1~5% with particle size distribution of 10 nm~0.1 µm (the following examples of the present invention are illustrated by using the conductive antistatic material by weight ratio of 5%).

In the first embodiment (Example 1) of the present invention, using polypropylene by weight ratio of 80% (melt flow rate is 5 g/10 min), powder (particle size: 0.3 µm) of optoelectronic material ($Sr_4Al_{14}O_{25}:Eu^{2+}, Dy^{3+}$) by weight ratio of 10%, powder (particle size 1 µm) of piezoelectric material (barium titanate ceramic) by weight ratio of 2%, powder (particle size: 1 µm) of thermoelectric material (containing $Al_2O_3$ by weight ratio of 35.92%, MgO by weight ratio of 33.86%, $Fe_2O$ by weight ratio of 16.10%, $TiO_2$ by weight ratio of 12.26% and $SiO_2$ by weight ratio of 2.86%) by weight ratio of 2%, powder (particle size: 0.31 µm) of catalyst material (containing gold by weight ratio of 30%/titanium oxide by weight ratio of 30%/zinc oxide by weight ratio of 40%) by weight ratio of 3% and EPDM (Mooney viscosity of 60) by weight ratio of 3%. The above-mentioned materials were kneaded by twin-screw with cooling air and granulated by granulation temperature of 180/200/210/220/230/240 degrees Celsius increasing gradually to produce a plurality of granular processing materials (with average particle size of about 5 mm), then the granular processing materials were mixed to be melt processing materials by a single screw at a mixing temperature of 200/210/220/230/240/250 by gradually increasing mode, and then the melt processing materials were made to be fibers by spinning, cooling at 25 degrees Celsius, hot-stretched at 100 degrees Celsius, and winding at 120 rpm. The results of the present invention are as followings.

The tensile strength and tear strength test results of example 1 are shown in Table 1. The tensile strength is gradually decreased accompanying with the increase of the content quantity of the optoelectronic material, the piezoelectric material, the thermoelectric material, the catalyst material and the EPDM, but remains in the required tensile strength. The optoelectronic material, the piezoelectric material, the thermoelectric material, the catalyst material and the EPDM added in the example 1 of the present invention are preferably 20~30% by weight ratio (the total weight ratio is 20% for the example in Table 1). Light storage effect ($Sr_4Al_{14}O_{25}:Eu^{2+}, Dy^{3+}$ for emitting blue and green light with wavelength of 488 nm) has an effectiveness lasting for 956 minutes. The effectiveness of uptake for chlorophyll and carotenoids is the highest at the wavelength of 400~520 nm, and the photosynthesis is the most affected. The light with 610~720 nm wavelength promotes photosynthesis and growth rate of plant (Such as $CaAl_{12}O_{19}:Mn^{4+}$ for emitting red light with wavelength of 656 nm)

TABLE 1

| Mesh | Danni number(d) | tensile | tear strength(longitude/latitude) |
|---|---|---|---|
| 50*50 | 200 | 57.5/50.5 (kgf/cm$^2$) | 9.9/11.9 (kg/cm$^2$) |

| Blue-Green light(488 nm)/Sample 20 g/after sunlight irradiation for 30 minutes | | | | | | |
|---|---|---|---|---|---|---|
| Time (min) | 0 | 10 | 30 | 60 | 120 | 956 (estimated brightness) |
| Storage brightness | 1850 | 122 | 32 | 18 | 5.6 | 0.32(mcd/m$^2$) |

The results of the far-infrared ray emissivity test of Example 1 are shown in Table 2. In the far-infrared ray emissivity test, the average emissivity of the far-infrared ray with wavelength of 3~15 µm at 50 degrees Celsius was 0.968. In the environment of 5 degrees Celsius, its average emissivity of far-infrared ray with wave length of 3~15 µm was 0.918.

TABLE 2

| Test item | Test Temperature | Result | Test way |
|---|---|---|---|
| far-infrared ray 3-15 µm average emissivity | 50° C. 5° C. | 0.968 0.918 | Infrared thermal radiometer, heat and electric coupling |

The results of the far-infrared experiment of Example 1 are described in Table 3. The far-infrared human physiological experiment of the fabricated woven fabric of the present invention was carried out and the temperature was raised to 2.9 degrees Celsius after 30 minutes on a health care fabric.

TABLE 3

| Test item | | Result °C. | |
|---|---|---|---|
| Blood flow of back of body | Before usage | 34.8 | * Human Physiology Experiment |
| | After sleeping on the sample for 30 mins | 45.7 | (1) Ambient temperature: room temperature. |
| | Difference amount (%) | 31.3 | (2) Subject: Male, 30 years old, 1 person. (3) Test time: |
| Temperature of back of body test by infrared thermal image | Before usage | 28.6 | Adaptation period: 20 minutes (before using sample) |
| | After sleeping on the sample for 30 mins | 31.5 | Test period: 30 minutes (after using sample) |
| | Difference amount (%) | 10.1% | (4) Subjects posture: Same postures at adaptation and test periods. (5) Measuring point: the center of the back |
| | | | * Measuring instrument |
| | | | (1) Laser flow imaging instrument: Moor Doppler Imager (LDI-V5.0) |
| | | | (2) Infrared digital thermal imager: Thermal Infrared-Ray digital camera |

The results of the negative ion experiments of Example 1 are shown in Table 4. The test was carried out with the woven fabric of the present invention, and 2858 anions (number/cc) in the air were increased under dynamic friction.

TABLE 4

| | result | | |
|---|---|---|---|
| Test item | Blank value | Sample | Test way |
| negative ion (number/cc) | 400 | 3258 | ITC-201A-temperature: 20° C.; humidity: 65% RH; Friction way: rotation speed: 400 rpm/min |

The results of the washing fastness test of Example 1 are shown in Table 5. The washing fastness test showed good fastness before and after the test, and the amount of negative ions was not reduced by washing.

TABLE 5

| Test item | Sample | Result | Test way |
|---|---|---|---|
| After washed 20 times: Dynamic-Average negative ion concentration | 1 | 2896 (Ions/cc) | Sample size = 10*10 CM (1 Sheet) |
| | 2 | 2988 (Ions/cc) | Wind speed: 5.15 CMM (182 CFM): 1 CMM (M³/min) = 35.3 CFM |
| | 3 | 2796 (Ions/cc) | |
| | 4 | 3258 (Ions/cc) | |
| | 5 | 2968 (Ions/cc) | |
| | 6 | 3568 (Ions/cc) | Negative ion release number analyzer (INTL: ITC-201A) Test object: relative negative ion content Test way for ion number: ion dynamic conversion method Time of determination of detection: 0.25 sec/1 cycle Test conditions: Temperature 25° C. Humidity 72% RH Water washing method: AATCC61-A2, washed 20 times |

The results of the test for the removal of contaminants by the fabric of Example 1 are shown in Table 6, Table 7 and Table 8. Test way: test at the both sides of the fabric which are the inlet and outlet respectively in an air channel, the size of the frame of the sample fabric is 24"*24"*2", the area of the sample fabric is 1M² (4 fabric sheets stacked and the area of each sheet is 1M²), Wind speed is 1M/S, temperature is 26 degrees Celsius, and humidity is 62% RH.

The total volatile organic Compound (TVOCS) removal test results in Example 1 are shown in Table 6.

TABLE 6

| | | TVOCS | | | | |
|---|---|---|---|---|---|---|
| Test No. Conc. | | n-Hexane ug/m³ | Benzene ug/m³ | Toluene ug/m³ | Hexamethyl cyclotrisiloxane ug/m³ | Octamethylcyclo-tetrasiloxane ug/m³ |
| | CAS NO. | 000110-54-3 | 000071-43-2 | 000108-88-3 | 000541-05-9 | 000556-67-2 |
| 1 | Inlet | 15.6 | 17.7 | 183.0 | 20.2 | 15.1 |
| | Outlet | 0 | 0 | 34.6 | 0 | 0 |
| | Eff. (%) | 100% | 100% | 81% | 100% | 100% |
| 2 | Inlet | 13.5 | 19.7 | 175.0 | 21.2 | 18.5 |
| | Outlet | 0 | 0 | 22.4 | 0 | 0 |
| | Eff. (%) | 100% | 100% | 87% | 100% | 100% |
| 3 | Inlet | 32.9 | 26.9 | 179.0 | 27.7 | 29.7 |
| | Outlet | 0 | 0 | 23.1 | 0 | 0 |
| | Eff. (%) | 100% | 100% | 87% | 100% | 100% |

The results of the indoor air quality (contaminant removal test) of Example 1 are shown in Table 7. The test equipment is referred to Table 7-1.

TABLE 7

| | | Contaminant removal test 1 | | | | | |
|---|---|---|---|---|---|---|---|
| Test No. Unit | | $CO_2$ ppm | CO ppm | $O_3$ ppm | TVOC ppm | HCHO ppm | RH % |
| 1 | Inlet | 558 | 0.8 | 0.09 | 0.658 | 0.025 | 65 |
| | Outlet | 482 | 0.3 | 0.02 | 0.288 | 0.015 | 64 |
| | Eff.(%) | 13.6% | 62.5% | 77.8% | 56.2% | 40.0% | 1.5% |
| 2 | Inlet | 649 | 0.8 | 0.09 | 0.636 | 0.028 | 62 |
| | Outlet | 565 | 0.2 | 0.03 | 0.288 | 0.015 | 64 |
| | Eff.(%) | 12.9% | 75.0% | 66.7% | 54.7% | 46.4% | −3.2% |
| 3 | Inlet | 576 | 0.8 | 0.09 | 0.668 | 0.032 | 64 |
| | Outlet | 514 | 0.2 | 0.02 | 0.276 | 0.015 | 65 |
| | Eff.(%) | 10.8% | 75.0% | 77.8% | 58.7% | 53.1% | −1.6% |

| | | Contaminant removal test 2 | | | | |
|---|---|---|---|---|---|---|
| Test No. | | Temp | $PM_{10}$ | $PM_{2.5}$ | Bacteria | Fungi |
| 1 | Inlet | 26.5 | 97 | 38 | 1617 | 153 |
| | Outlet | 26.4 | 73 | 15 | 33 | 17 |
| | Eff.(%) | 0.4% | 24.7% | 60.5% | 98.0% | 88.9% |
| 2 | Inlet | 27.4 | 93 | 42 | 1708 | 185 |
| | Outlet | 27.3 | 66 | 16 | 83 | 25 |
| | Eff.(%) | 0.4% | 29.0% | 61.9% | 95.1% | 86.5% |
| 3 | Inlet | 27.4 | 59 | 66 | 1008 | 127 |
| | Outlet | 27.2 | 43 | 20 | 17 | 8 |
| | Eff.(%) | 0.7% | 27.1% | 69.7% | 98.3% | 93.7% |

TABLE 7-1

| Item | Analyzer Model | Resolution | Range |
|---|---|---|---|
| $CO_2$ | PPMonitor SAS | 1 ppm | 0~5000 ppm |
| CO | PPMonitor SAS | 0.1 ppm | 0~100 ppm |
| $O_3$ | PPMonitor SAS | 0.01 ppm | 0~1 ppm |
| TVOC | ppb RAE + PGM-7240 | 10% of reading or 20 ppb | 0~9999 ppb |
| HCHO | PPMonitor SAS | 0.011 ppm | 0~10 ppm |
| RH | PPMonitor SAS | 0.01% | 0-100% |
| Temp | PPMonitor SAS | 0.01° C. | −40° C. to 128° C. |
| $PM_{10}$ | TSI 8520 DustTrak | ±0.1% of reading or ±0.001 mg/m$^3$ | 0.001~100 mg/m$^3$ |
| $PM_{2.5}$ | TSI 8520 DustTrak | ±0.1% of reading or ±0.001 mg/m$^3$ | 0.001~100 mg/m$^3$ |
| Bacteria | BURKARD | N/A | N/A |
| Fungi | BURKARD | N/A | N/A |

Table 8 shows the results of the test for the positive and negative ion contaminant removal efficiency in air for the Example 1.

TABLE 8

| | | Cation & Anion | | | | | |
|---|---|---|---|---|---|---|---|
| Test No. Unit | | F$^-$ ppbv | Cl$^-$ ppbv | $NO_3^-$ ppbv | $PO_4^{3-}$ ppbv | $SO_4^{2-}$ ppbv | $NH_4^+$ ppbv |
| 1 | Inlet | 0.135 | 0.212 | 0.39 | <0.012 | 0.349 | 6.84 |
| | Outlet | <0.012 | 0.067 | 0.043 | <0.012 | 0.132 | 5.47 |
| | Eff.(%) | 100.0% | 68.4% | 89.0% | N/A | 62.2% | 20.0% |
| 2 | Inlet | 0.135 | 0.15 | 0.112 | <0.012 | 0.287 | 6.71 |
| | Outlet | <0.012 | 0.054 | 0.011 | <0.012 | 0.112 | 5.32 |
| | Eff.(%) | 100.0% | 64.0% | 90.2% | N/A | 61.0% | 20.7% |
| 3 | Inlet | 0.135 | 0.221 | 0.84 | <0.012 | 0.271 | 6.23 |
| | Outlet | <0.012 | 0.081 | 0.058 | <0.012 | 0.063 | 5.11 |
| | Eff.(%) | 100.0% | 63.3% | 93.1% | N/A | 76.8% | 18.0% |

Table 9 shows the Antibacterial test results of Example 1 which has the Antibacterial rate of 99.9% (R %).

TABLE 9

| | Test way: ASTM E2149-01 | | |
|---|---|---|---|
| Bacteria | Number of Bacteria after 0 hour (CFU/ml) | Number of Bacteria after 1 hour (CFU/ml) | Antibacterial rate (%) |
| *Klebsiella pneumoniae* Veterans | 3.2 × 10$^5$ 2.8 × 10$^5$ | <5.0 <5.0 | 99.9 99.9 |
| *Escherichia coli* | 3.5 × 10$^5$ | <5.00 | 99.9 |
| *Staphylococcus aureus* | 5.6 × 10$^5$ | <5.0 | 99.9 |
| Resistant *Staphylococcus aureus* (MRSA) | 2.1 × 10$^5$ | <5.0 | 99.9 |
| *Pseudomonas aeruginosa* | 5.2 × 10$^5$ | <5.0 | 99.9 |
| *Bacillus subtilis* | 3.6 × 10$^5$ | <5.0 | 99.9 |

Table 10 shows the mildew test results.

TABLE 10

| | Status and degree of growth of bacteria on the sample | | Way of judge | |
|---|---|---|---|---|
| Test item and way for mildew JIS Z2911 | Degree | Growth status of Sample | Degree: | status of growth |
| *Aspergillus niger* | 0 | No growth | 0: | No growth |
| Bulb shell | 0 | No growth | 1 | Growth not over ⅓ area |
| *Cercospora* | 0 | No growth | 2 | Growth over ⅔+12area |
| *Penicillium* | 0 | No growth | | |
| White ringworm | 0 | No growth | | |

In the second embodiment (Example 2) of the present invention, using polypropylene by weight ratio of 80% (melt flow rate is 5 g/10 min), powder (particle size: 0.3 μm) of optoelectronic material ($Sr_4Al_{14}O_{25}$:$Eu^{2+}$, $Dy^{3+}$) by weight ratio of 2%, powder (particle size 1 μm) of piezoelectric material (barium titanate ceramic) by weight ratio of 2%, powder (particle size: 1 μm) of thermoelectric material (containing $Al_2O_3$ by weight ratio of 35.92%, MgO by weight ratio of 33.86%, $Fe_2O$ by weight ratio of 16.10%, $TiO_2$ by weight ratio of 12.26% and $SiO_2$ by weight ratio of 2.86%) by weight ratio of 2%, powder (particle size: 0.3 μm) of catalyst material (containing gold by weight ratio of 30%/titanium oxide by weight ratio of 30%/zinc oxide by weight ratio of 40%) by weight ratio of 3%, EPDM (Mooney viscosity of 60) by weight ratio of 3%, and plant essential oil material (containing Eucalyptus oil by weight ratio of 20%, lemon oil by weight ratio of 30% and tea tree oil by weight ratio of 50%) by weight ratio of 8%. The above-mentioned materials were kneaded by twin-screw with cooling air and granulated by granulation temperature of 180/200/210/220/230/240 degrees Celsius increasing gradually to produce a plurality of granular processing materials (with average particle size of about 5 mm), then the granular processing materials were mixed to be melt processing materials by a single screw at a mixing temperature of 200/210/220/230/240/250 by gradually increasing mode, and then the melt processing materials were made to be fibers by spinning, cooling at 25 degrees Celsius, hot-stretched at 100 degrees Celsius, and winding at 120 rpm.

Table 11 shows the physical properties of the fabric of Example 2.

TABLE 11

| Mesh | Danni number (d) | Area of Sample | Weight of sample |
|---|---|---|---|
| 50*50 | 200 | 1 m² | 98 g |

Table 12 shows the test results of avoidance rate for the dust mite for Example 2 which having the avoidance rate of 90.3%.

TABLE 12

| Test item | | Control group | Control group | Test way |
|---|---|---|---|---|
| European dust mites | 1 | 2015 | 236 | JIS L1920: 2007 |
| | 2 | 1897 | 185 | Avoidance test |
| | 3 | 1998 | 175 | Invasion prevent way |
| | 4 | 1975 | 182 | |
| | 5 | 1895 | 166 | |
| | Average | 1956 | 189 | |
| | Avoidance rate (%) | 90.3% | | |

Table 13 shows the test results of the measurement of the essential oil component by gas chromatography mass spectrometer (GC/MS) for Example 2. The sample was positioned in 1 cubic meters of closed box and processed with test operation for 1 hour. Then we obtained the result of the essential oil component shown in Table 13. The test method is by the gas chromatography mass spectrometer (GC/MS).

TABLE 13

| NO. | Compounds | CAS NO. | Test result | Test limit | Unit |
|---|---|---|---|---|---|
| 1 | α-terpipnen | 000099-86-5 | 21.30 | 1 | mg/kg |
| 2 | terpinen-4-ol | 0000562-74-3 | 212.58 | 1 | mg/kg |
| 3 | α-Pinene | 000080-56-8 | 46.25 | 1 | mg/kg |
| 4 | 1,2,4-Trimethylbenzene | 000095-63-6 | 1.20 | 1 | mg/kg |
| 5 | γ-Terpinen | 000099-85-4 | 386.75 | 1 | mg/kg |
| 6 | Ethylbenzene | 000100-41-4 | 2.05 | 1 | mg/kg |
| 7 | terpinolene | 000586-62-9 | 9.88 | 1 | mg/kg |
| 8 | n-Decane | 000124-18-5 | 3.56 | 1 | mg/kg |
| 9 | β-Pinene | 000127-91-3 | 12.50 | 1 | mg/kg |
| 10 | Limonene | 000138-86-3 | 288.16 | 1 | mg/kg |
| 11 | α-Cedrene | 000469-61-4 | 18.90 | 1 | mg/kg |
| 12 | Thujopsene | 000470-40-6 | 12.39 | 1 | mg/kg |
| 13 | 1,8-Cineole | 000470-82-6 | 298 | 1 | mg/kg |
| 14 | n-Undecane | 001120-21-4 | 2.68 | 1 | mg/kg |
| 15 | 4-methyl-Decane | 002847-72-5 | 2.01 | 1 | mg/kg |
| 16 | α-Thujene | 002867-05-2 | 1.01 | 1 | mg/kg |
| 17 | γ-Muurolene | 030021-74-0 | 5.67 | 1 | mg/kg |
| 18 | Benzene,1-methyl-4- | 000535-77-3 | 25.56 | 1 | mg/kg |

Table 14 shows the results of the analysis of pollutant removal in air for Example 2. The sample with area of 1 m² was positioned in 1 m³ closed space under 6.5 CMM air volume for the test of removal number of contaminant per minute.

TABLE 14

| Item (in the air) | Sample | Air volume | Removal number/min | Unit | Test way |
|---|---|---|---|---|---|
| Total carbon monoxide concentration | 1 m² | 6.5 CMM | 68 | ppm | JEM1467 |
| Total carbon dioxide concentration | 1 m² | 6.5 CMM | 50 | ppm | JEM1467 |
| Total ozone concentration | 1 m² | 6.5 CMM | 0.4 | ppm | JEM1467 |
| Total acetic acid concentration | 1 m² | 6.5 CMM | 125 | ng | JEM1467 |
| Total formaldehyde concentration | 1 m² | 6.5 CMM | 350 | ng | JEM1467 |
| Total acetaldehyde concentration | 1 m² | 6.5 CMM | 250 | ng | JEM1467 |
| Total ammonia concentration | 1 m² | 6.5 CMM | 15.6 | ng | JEM1467 |
| Total volatile organic compounds | 1 m² | 6.5 CMM | 450 | ng | JEM1467 |
| Total suspended particulates (10 μm) | 1 m² | 6.5 CMM | 1.35 | mg/m3 | JEM1467 |
| Total suspended particulates (2.5 μm) | 1 m² | 6.5 CMM | 1.98 | mg/m3 | JEM1467 |
| Total bacterial concentration | 1 m² | 6.5 CMM | 16 | CFU/m3 | JEM1467 |
| Total fungal concentration | 1 m² | 6.5 CMM | 18 | CFU/m3 | JEM1467 |

In the third embodiment (Example 3) of the present invention, using polypropylene by weight ratio of 80% (melt flow rate is 5 g/10 min), powder (particle size: 0.3 μm) of optoelectronic material ($Sr_4Al_{14}O_{25}:Eu^{2+}, Dy^{3+}$) by weight ratio of 2%, powder (particle size 1 μm) of piezoelectric material (barium titanate ceramic) by weight ratio of 2%, powder (particle size: 1 μm) of thermoelectric material (containing $Al_2O_3$ by weight ratio of 35.92%, MgO by weight ratio of 33.86%, $Fe_2O$ by weight ratio of 16.10%, $TiO_2$ by weight ratio of 12.26% and $SiO_2$ by weight ratio of 2.86%) by weight ratio of 2%, powder (particle size: 0.3 μm) of catalyst material (containing gold by weight ratio of 30%/titanium oxide by weight ratio of 30%/zinc oxide by weight ratio of 40%) by weight ratio of 3%, EPDM (Mooney viscosity of 60) by weight ratio of 3%, plant essential oil material (containing Eucalyptus oil by weight ratio of 20%, lemon oil by weight ratio of 30% and tea tree oil by weight ratio of 50%) by weight ratio of 3%, fireproof materials with particle size about 0.5 μm (containing magnesium hydroxide by 5 weight ratio of 90% and Antimony trioxide by weight ratio of 10%) by weight ratio of 10%, and conductive antistatic materials with average particle diameter about 0.2 μm (conductive carbon black) by weight ratio of 5%. The above-mentioned materials were kneaded by twin-screw with cooling air and granulated by granulation temperature of 180/200/210/220/230/240 degrees Celsius increasing gradually to produce a plurality of granular processing materials (with average particle size of about 5 mm), then the granular processing materials were mixed to be melt processing materials by a single screw at a mixing temperature of 200/210/220/230/240/250 by gradually increasing mode, and then the melt processing materials were made to be fibers by spinning, cooling at 25 degrees Celsius, hot-stretched at 100 degrees Celsius, and winding at 120 rpm.

Table 15 shows the test results of toxic gas content for Example 3 which meet the requirements. The Toxic Gas value of this report refers to the toxic gas content produced by the combustion test for 4 minutes. ABD0031 (2005) ISSUE compliances F requirements which is tested by Detection tube and measured to have the result with HF<100, HCl<150, HCN<150, $SO_2$<100, $XO_2$<100 and CO<1000.

TABLE 15

| Sample item | Sample Size (mm) (L*W*T) | Toxic gas (ppm) | | | | | |
|---|---|---|---|---|---|---|---|
| | | HCl | HF | $SO_2$ | $XO_2$ | HCN | CO |
| Sample-1 | 75.0*74.0*2.80 | 1 | 0 | 0 | 2 | 1 | 300 |
| Sample-2 | 75.0*75.0*2.51 | 1 | 0 | 0 | 1 | 1 | 200 |
| Sample-3 | 73.0*75.0*2.48 | 0.5 | 0 | 0 | 2 | 2 | 250 |
| Average | | 0.8 | 0 | 0 | 1.7 | 1.3 | 250.0 |

Table 16 shows the results of Horizontal Combustion Test for Example 3 which compliance with the requirement (referring to. FAR 25.853 (b), (Amdt. 25-116, 2004) & Appendix F Par I (a) (1) (ii)). Flame time is less than or equal to 15 Secs, Drip flame time is less than or equal to 5 Secs; Burn length is less than or equal to 8 inches (203.2 mm).

TABLE 16

| | | Combustion status | | | | | |
|---|---|---|---|---|---|---|---|
| Sample item | Sample Size (mm)(L*W*D) | Flame time (sec) | Average (sec) | Drip flame time (sec) | Average (sec) | Burn length in(mm) | Average in(mm) |
| Sample-1 | 305.0*76.0*3.28 | 0 | 0 | 0 | 0 | 5(127.0) | 4(114.3) |
| Sample-2 | 305.0*76.0*3.44 | 0 | | 0 | | 4(114.3) | |
| Sample-3 | 305.0*76.0*3.15 | 0 | | 0 | | 4(101.6) | |

Table 17 shows the results of the vertical combustion test for Example 3 which meet the requirements (referring to Appendix F Amdt. 25-111 of FAR 25.853, Te(10)=te(11.5)−te(1.5)).

TABLE 17

| | | Flame status | | | | | | |
|---|---|---|---|---|---|---|---|---|
| Sample Item | Sample Size (mm)(L*W*D) | te(1.5) (sec) | te(11.5) (sec) | te(10) (sec) | te(f) (sec) | d(f) (in) (mm) | Burn speed (in/min) (mm/min) | Average in(mm) (mm/min) |
| Sample1 | 305.0*76.0*3.77 | 0 | 0 | 0 | 0 | 1/42 | 0 | 0 |
| Sample2 | 305.0*76.0*3.02 | 0 | | 0 | | 1/4 | 0 | |
| Sample3 | 305.0*76.0*2.56 | 0 | | 0 | | 1/4 | 0 | |

Table 18 shows the test results Smoke concentration for Example 3 which show Compliance. $D_m$ is the maximum value of the measured smoke concentration for the sample within 4 minutes test. ABD0031 (2005) issues F regulatory requirements that the maximum smoke concentration within 4 minutes of test time in flame or flawless test conditions should not exceed the gauge values listed in Table 19.

TABLE 18

| | | Test result | | |
|---|---|---|---|---|
| Sample item | Sample Size (mm) (L*W*D) | Test value ($D_m$) | Average ($D_m$) | Time of Maximum $D_m$ |
| Sample-1 | 74.0*75.0*2.29 | 22 | 19 | 4'00" |
| Sample-1 | 73.0*73.0*2.96 | 17 | | 4'00" |
| Sample-1 | 75.0*73.0*2.99 | 18 | | 3'58" |

TABLE 19

| Test components | $D_m$ |
|---|---|
| Airducting | 100 |

Table 20 shows the result of antistatic test for Example 3 which shows R=5.8×10$^5$Ω.

TABLE 20

| Test item | Result | Test way and condition |
|---|---|---|
| Antistatic test - Surface Resistivity | R = 5.8 × 10$^5$ Ω/cm | EN 1149-2: 1996 |

The embodiments as described above are only possible embodiments of the present invention, which are not intended to limit the scope of the invention, and where equivalents are made will meet the contents, features and spirit of the invention as set forth in the following claims. The present invention is specifically defined in the structural features of the claims, which is not found in the prior arts, and has practicality and progress to be allowable for patent.

NUMBERED ELEMENTS fiber 10; ridge 11; curved depression 12; fabric 20; optoelectronic material 30; piezoelectric material 31; thermoelectric material 32; catalyst material 33.

What is claimed is:

1. A method for manufacturing environment-controlling fibers comprising the steps of:
preparing a specific amount of processing material including a specific amount of polyolefin as a base material, a specific amount of optoelectronic material, a specific amount of piezoelectric material, a specific amount of thermoelectric material, a specific amount of rubber elastic material and a specific amount of catalyst material;
melting and mixing the specific amount of processing material to be a specific amount of granular processing material by an air-cooled granulation equipment under a temperature condition from 160 to 350 degrees Celsius; and
melting and drawing the specific amount of granular processing material to obtain the fibers, so that the specific amount of optoelectronic material can receive energies outside the fibers to produce optoelectronic effect, the specific amount of piezoelectric material can receive energies outside the fibers to produce piezoelectric effect, the specific amount of thermoelectric material can receive energies outside the fibers to produce thermoelectric effect, and the specific amount of catalyst material can be resonated by the optoelectronic effect, the thermoelectric effect and the piezoelectric effect to increase amplitudes of the energies so as to increase the catalysis activity of the catalyst material.

2. The method as claimed in claim 1, wherein the specific amount of polyolefin is by weight ratio of 70~95%; the specific amount of optoelectronic material is by weight ratio of 1%~10%; the specific amount of piezoelectric material is by weight ratio of 1%~5%, the specific amount of thermoelectric material is by weight ratio of 1%~5% and the specific amount of catalyst material is by weight ratio of 1%~5% and the specific amount of rubber elastic material is by weight ratio of 1%~5%.

3. The method as claimed in claim 1, wherein the specific amount of processing material further includes amount of natural plant essential oil by weight ratio of 1~10%; the specific amount of rubber elastic material is by weight ratio of 1~5%; the specific amount of polyolefin is by weight ratio of 65~94%; the specific amount of optoelectronic material is by weight ratio of 1~5%; the specific amount of piezoelectric material is by weight ratio of 1~5%, the specific amount of thermoelectric material is by weight ratio of 1~5% and the specific amount of catalyst material is by weight ratio of 1~5%.

4. The method as claimed in claim 1, wherein the specific amount of processing material further includes amount of natural plant essential oil by weight ratio of 1~5%, amount of fireproof material by weight ratio of 1~10% and amount of conductive antistatic material by weight ratio of 1~5%; the specific amount of rubber elastic material is by weight ratio of 1~5%; the specific amount of polyolefin is by weight ratio of 55~92%; the specific amount of optoelectronic material is by weight ratio of 1~5%; the specific amount of piezoelectric material is by weight ratio of 1~5%, the specific amount of thermoelectric material is by weight ratio of 1~5% and the specific amount of catalyst material is by weight ratio of 1~5%.

5. The method as claimed in claim 4, wherein the fireproof material is selected at least one from the group consisting of magnesium hydroxide, antimony trioxide, red phosphorus, molybdenum compounds, zinc borate, zinc stannate, decabromodiphenyl oxide, octabromo-ether, organic silicone and carbon black; the conductive antistatic material is selected from the group consisting of conductive carbon black, polyether, quaternary ammonium salt, sulfonate, betaine, carbon fiber, metal fiber, nickel-plated metal carbon fiber and nano carbon nanotube.

6. The method as claimed in any one of claims 1 to 5, wherein the polyolefin material is selected from the group consisting of polypropylene and polyethylene; the optoelectronic material is selected at least one from the group consisting of $(SrBaMg)_3Si_2O_7$, $LiAl_5O_8O:Mn^{4+}$, $CaAl_2O_4:Eu^{2+}, Dy^{3+}$, $CaAl_{12}O_{19}:Mn^{4+}$, $SrAl_2O_4:Eu^{2+}, Dy^{3+}$, $Sr_4Al_{14}O_{25}:Eu^{2+}, Dy^{3+}$, $SrAl_{12}O_{19}:Eu^{2+}, Dy^{3+}$, $BaMg_2Al_{16}O_{27}$, $CeMgAl_{11}O_{19}$, $MgAl_2O_4$, $GdAlO_3$ and $MgGa_2O_4$; the piezoelectric material is selected at least one from the group consisting of quartz, cadmium sulfide, zinc oxide, aluminum nitride, ferroelectric crystal, barium titanate crystal, lithium niobate, tantalum niobate, barium niobate crystal, deuterium lead phosphate, bismuth titanate crystals, barium titanate ceramics, lead zirconate titanate (PZT); the thermoelectric material is selected at least one from the group consisting of $Al_2O_3$, $ZrO_2$, $MgO$, $TiO_2$, $SiO_2$, $ZrC$, $SiC$, $B_4C$, $TaC$, $TiB_2$, $ZrB_2$, $CrB_2$, $TiSi_2$, $MoSi_2$, $WSi_2$, $Si_3N_4$, $Fe_2O$, bamboo charcoal, prepared long charcoal, Maifan stone, Guiyang stone, volcanic rocks and jade; the catalyst material is selected at least one from the group consisting of gold, platinum, palladium, rhodium, Copper, titanium, tungsten, zinc, manganese, germanium, bismuth, ruthenium, iridium, molybdenum, chromium, lanthanum, cerium, praseodymium, neodymium, Promethium, carbon nanotubes, germanium oxide, zinc oxide, Titanium, alumina, iron oxide, palladium oxide, magnesium oxide, zirconium oxide, nickel oxide, tin oxide, manganese oxide, chromium oxide, cerium oxide, neodymium oxide and yttrium oxide.

7. The method as claimed in claim 1, wherein the temperature condition is gradually increased by a margin of at least 10 degrees Celsius.

8. The method as claimed in claim 1, wherein when the polyolefin is polypropylene, the temperature condition is from 160 to 250 degrees Celsius; when the polyolefin is polyethylene, the temperature condition from 260 to 350 degrees Celsius.

9. The method as claimed in claim 8, wherein the temperature condition is gradually increased by a margin of at least 10 degrees Celsius.

* * * * *